(12) United States Patent
Mault

(10) Patent No.: US 6,571,200 B1
(45) Date of Patent: May 27, 2003

(54) MONITORING CALORIC EXPENDITURE RESULTING FROM BODY ACTIVITY

(75) Inventor: James R. Mault, Evergreen, CO (US)

(73) Assignee: Healthetech, Inc., Golden, CO (US)

( * ) Notice: Subject to any disclaimer, the term of this patent is extended or adjusted under 35 U.S.C. 154(b) by 331 days.

(21) Appl. No.: 09/684,440

(22) Filed: Oct. 10, 2000

Related U.S. Application Data

(60) Provisional application No. 60/158,554, filed on Oct. 8, 1999, and provisional application No. 60/225,101, filed on Aug. 14, 2000.

(51) Int. Cl.$^7$ .................................................. G06F 3/00
(52) U.S. Cl. ...................... 702/182; 702/131; 702/183; 702/189
(58) Field of Search .......................... 702/99, 130, 131, 702/182, 183, 189; 482/9; 600/300, 531

(56) References Cited

U.S. PATENT DOCUMENTS

| | | | |
|---|---|---|---|
| 3,401,683 A | 9/1968 | Webb et al. ................ 128/2.07 |
| 3,972,038 A | 7/1976 | Fletcher et al. ......... 340/189 M |
| 4,117,834 A | 10/1978 | McPartland et al. ........ 128/2 S |
| 4,224,952 A | 9/1980 | Sidorenko et al. .......... 128/782 |
| 4,299,235 A | 11/1981 | Cohen ......................... 128/718 |
| 4,353,375 A | 10/1982 | Colburn et al. ............. 128/782 |
| 4,566,461 A | 1/1986 | Lubell et al. ................ 128/668 |
| 4,803,625 A | 2/1989 | Fu et al. ................. 364/413.03 |
| 4,828,257 A | 5/1989 | Dyer et al. .................. 272/129 |
| 4,855,942 A | 8/1989 | Bianco ........................ 364/561 |
| 4,966,155 A | 10/1990 | Jackson ....................... 128/671 |
| 5,263,491 A | 11/1993 | Thornton ..................... 128/774 |
| 5,485,402 A | 1/1996 | Smith et al. ................. 364/566 |
| 5,524,637 A | 6/1996 | Erickson ...................... 128/779 |
| 5,705,735 A | 1/1998 | Acorn .......................... 73/23.3 |
| 5,810,722 A | 9/1998 | Heikkila ...................... 600/300 |
| 5,954,640 A | 9/1999 | Szabo ......................... 600/300 |
| 5,989,188 A | 11/1999 | Birkhoelzer et al. ........ 600/300 |
| 6,013,007 A | 1/2000 | Root et al. ...................... 482/8 |
| 6,013,009 A * | 1/2000 | Karkanen ....................... 482/9 |
| 6,030,342 A | 2/2000 | Amano et al. .............. 600/301 |
| 6,045,513 A | 4/2000 | Stone et al. ................. 600/508 |
| 6,059,732 A * | 5/2000 | Orr et al. ..................... 600/532 |
| 6,077,193 A | 6/2000 | Buhler et al. ................... 482/8 |
| 6,083,006 A | 7/2000 | Coffman ...................... 434/127 |
| 6,095,949 A | 8/2000 | Arai .............................. 482/4 |
| 6,135,107 A | 10/2000 | Mault .................... 128/204.23 |
| 6,135,950 A | 10/2000 | Adams ........................ 600/300 |
| 6,135,951 A | 10/2000 | Richardson et al. ........ 600/300 |
| 6,309,360 B1 * | 10/2001 | Mault ......................... 600/531 |
| 6,468,222 B1 * | 10/2002 | Mault et al. ................ 600/531 |

OTHER PUBLICATIONS

Peter H. Dana, Global Position System, Department of Geography, University of Texas at Austin, 1994, pp. 1–13.*

* cited by examiner

Primary Examiner—Marc S. Hoff
Assistant Examiner—Felix Suarez

(57) ABSTRACT

Apparatus for monitoring the caloric expenditure rate of a subject, comprising: a caloric expenditure rate detector for detecting and measuring the caloric expenditure rate of the subject; a body activity detector for detecting and measuring the body activity of the subject; and a processor for storing a measured caloric expenditure rate and a concurrently measured body activity for each of a plurality of different body activities and activity rates, to enable each subsequently detected body activity measurement to be converted to the caloric expenditure rate of the respective subject.

25 Claims, 3 Drawing Sheets

MONITORING CALORIC EXPENDITURE RESULTING FROM BODY ACTIVITY

RELATED APPLICATION

This application is related to provisional application 60/158,554 filed Oct. 8, 1999 and provisional application 60/225,101 filed Aug. 14, 2000, claims the priority date of those applications, and incorporates the contents of those applications herein in their entireties.

FIELD AND BACKGROUND OF THE INVENTION

This application relates to an apparatus and method for monitoring the caloric expenditure rate of a subject, and also for monitoring the caloric diet of the subject.

Good personal health and fitness in general, and weight management in particular, requires some form of monitoring the caloric diet, both the caloric intake and the caloric expenditure. Many monitoring techniques and devices have been proposed, for example as described in U.S. Pat. No. 6,013,009, and the many patents discussed therein, as well as in U.S. Pat. No. 5,891,042.

U.S. Pat. No. 5,891,042 discloses a fitness monitoring device including a body motion detector (e.g. a pedometer) which measures body motion (i.e. physical activity) of the subject, and a heart rate detector which measures the heart rate, and thereby the exertion level of the subject. The device further includes a processor which may process this information according to a plurality of different modes, one of which is a calorie mode, for converting these measurements into caloric expenditure.

U.S. Pat. No. 6,013,009 discloses a heart rate monitoring system which includes a sub-unit utilizing physical activity data (e.g., walking or running) to calculate a rate of calories burned per pound for each test exercise. The calculation is performed using a pre-programmed formula based on statistical data accumulated from several thousand sample adults.

My prior U.S. Pat. Nos. 4,917,108; 5,038,792; 5,178,155; 5,179,958; and 5,836,300, all of which are hereby incorporated by reference, disclose another system for measuring caloric expenditure using indirect calorimetry, by measuring the metabolism of the subject. Such a system includes a respiratory gas analyzer which detects inhalations and exhalations of the subject, analyzes the oxygen consumption, and produces a caloric expenditure rate measurement from the analysis of the oxygen consumption. Such a technique has a number of advantages for measuring caloric expenditure as described in those patents.

OBJECT AND BRIEF SUMMARY OF THE PRESENT INVENTION

An object of the present invention is to provide apparatus and method for monitoring the caloric expenditure rate of a subject which is particularly, but not exclusively, useful with the indirect calorimeter technique described in my above U.S. patents in order to obtain many of the advantages provided by such a technique. Another object of the invention is to provide apparatus and method for monitoring the caloric expenditure rate of a subject, which apparatus and method are more closely tailored to the individual subject, rather than to statistical samples, and therefore are more capable of attaining higher accuracy than previously known techniques, such as described in U.S. Pat. No. 6,013,009.

Another object of the invention is to provide apparatus and method for monitoring the caloric expenditure rate of a subject according to a technique which is more flexible than previously known techniques, since it enables the individual subject to select one or more of a wide variety of exercises the individual wishes to perform and to measure the caloric expenditure rate applicable to the exercise and exercise rate selected by the subject.

According to one aspect of the present invention, there is provided apparatus for monitoring the caloric expenditure rate of a subject, comprising: a caloric expenditure rate detector for detecting and measuring the caloric expenditure rate of the subject; a body activity detector for detecting and measuring the body activity of the subject; and a processor for storing a measured caloric expenditure rate and a concurrently measured body activity for each of a plurality of different body activities and activity rates, to enable each subsequently detected body activity measurement to be converted to the caloric expenditure rate of the respective subject.

According to further features in the preferred embodiment of the invention described below, the processor is programmable to operate in: a test mode, in which the processor measures and stores a caloric expenditure rate for each body activity; and an operational mode, in which the processor converts each subsequently detected body activity measurement to the corresponding caloric expenditure rate stored during the test mode.

As indicated earlier, the apparatus is particularly, but not exclusively, useful in the indirect calorimetry technique for measuring caloric expenditure as described in the above-cited U.S. patents, in which case the caloric expenditure rate detector would be a respiratory gas analyzer which detects inhalations and exhalations of the subject, analyzes the oxygen consumption, and produces said caloric expenditure rate measurement therefrom.

According to still further features in the described preferred embodiment, the body activity detector produces a body activity measurement also when the body of the subject is relatively at rest, to enable a personal correlation factor also to be computed and stored during the test mode corresponding to a relatively at rest body condition of the subject, and to be used in the operational mode for modifying the caloric expenditure rate measured when the subject's body is relatively at rest.

The body activity detector may detect physical activities of a subject including walking and running at different rates, and/or physical exertions of the subject, e.g. as indicated by the heart rate of the subject.

The body activity detector may comprise a clock and a position detection system such as a global positioning system (GPS). By storing the user's position and time at intervals along a walking, running or biking route, the user's speed may be calculated and correlated with previous measurements of caloric expenditure while performing the exercise at various rates to determine the caloric expenditure over the route.

According to another aspect of the present invention, there is provided a method of monitoring the caloric expenditure of a subject, comprising:

A. equipping the subject with: (1) a calorie expenditure rate detector for producing a caloric expenditure rate measurement of the subject, and (2) a body activity detector for producing a body activity measurement of the subject;

B. during a test mode: (1) utilizing the detectors for producing the caloric expenditure rate measurement and the body activity measurement while the subject is undergoing a plurality of different body activities and at different rates, and (2) storing the correlation between the two measurements for each of the body activities; and C. during an operational mode:
 (1) utilizing the body activity detector for producing a body activity measurement;
 (2) retrieving the corresponding caloric expenditure rate measurement stored for the respective body activity; and
 (3) utilizing the retrieved caloric expenditure rate measurement as the measurement of the caloric expenditure rate in monitoring the caloric expenditure of the subject.

According to a still further aspect of the present invention, there is provided apparatus for monitoring the caloric diet of a subject, comprising:

a caloric expenditure rate detector for detecting and measuring the caloric expenditure rate of a subject;

a body activity detector for detecting and measuring the body activity of the subject; and a processor for:
 (a) processing a measured caloric expenditure rate and a concurrently measured body activity to compute a personal correlation factor for each of a plurality of different body activities;
 (b) modifying a subsequently measured body activity by the personal correlation factor to determine the caloric expenditure of the subject at the time the body activity is measured;
 (c) integrating the caloric expenditure rate over a period of time to produce a total caloric expenditure; and
 (d) producing a balance of the total caloric expenditure minus caloric intake inputted into the apparatus over the period of time.

It will thus be seen that the present invention involves the actual measurement of caloric expenditure rate of a subject simultaneously with the measurement of the subject's body activity in order to produce a personal correlation factor which may thereafter be used to compute the actual caloric expenditure by that subject to achieve the particular body activity involved when the body activity is measured. Such a technique, therefore, enables attaining high accuracy for the respective subject and is compatible with the exercises selected by the subject.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
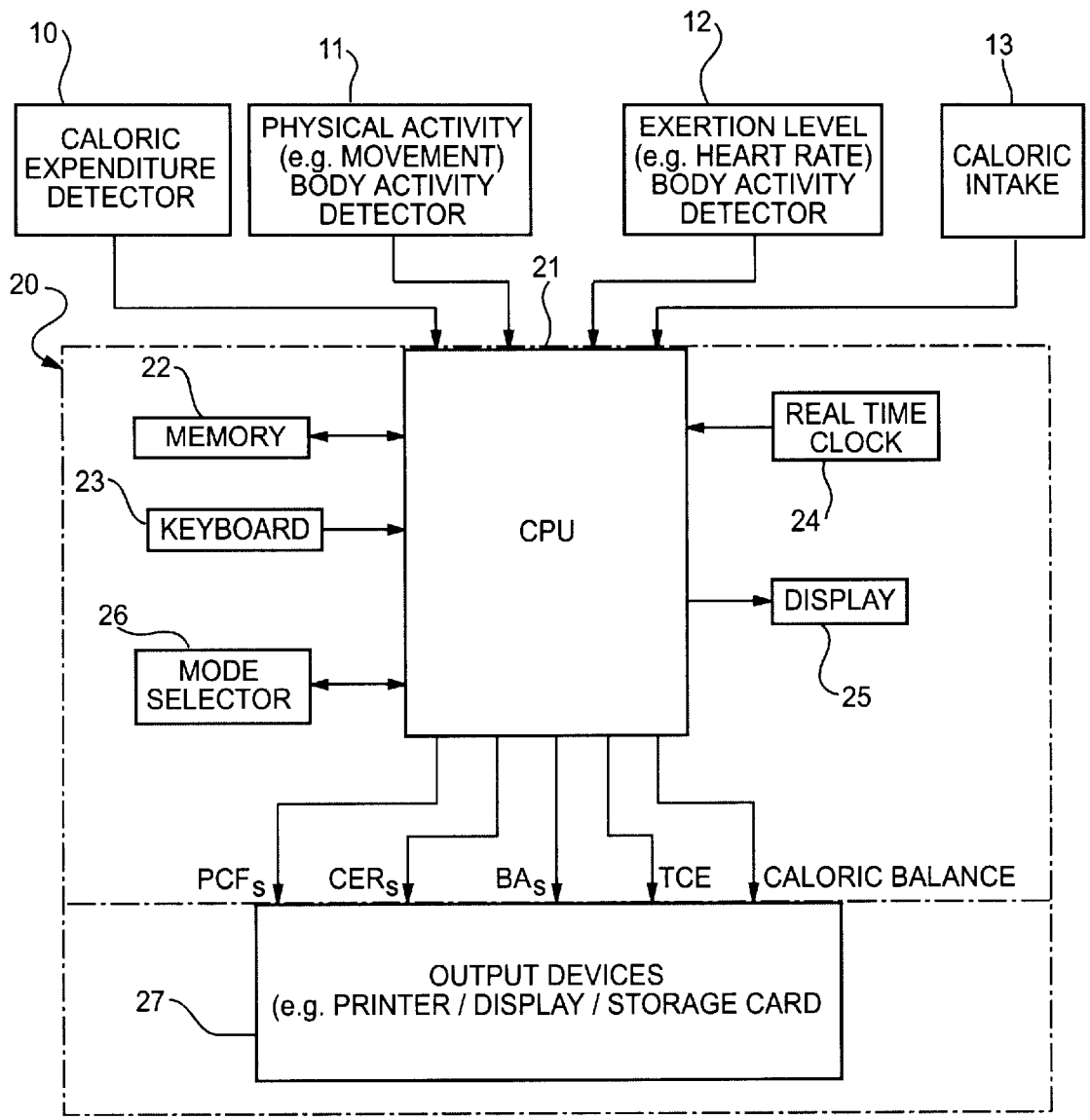
FIG. 1 is a block diagram illustrating one form of apparatus constructed in accordance with the present invention.

FIG. 1 is a block diagram illustrating one form of apparatus constructed in accordance with the present invention for monitoring the caloric expenditure rate of a subject, whenever desired, e.g. when doing certain exercises or when relatively inactive. The apparatus illustrated in FIG. 1 also provides for inputting the caloric intake of the subject, e.g. in the form of calories or foods converted to calories by the apparatus, and therefore may also be used for monitoring the caloric diet of a subject to produce a balance of caloric intake minus caloric expenditure over any desired period of time.

The apparatus illustrated in FIG. 1 includes a caloric expenditure detector 10; a physical activity detector 11; and an exertion level detector 12. If the apparatus is also to be used for monitoring the caloric diet of the individual, it would also include a caloric intake input 13.

The caloric expenditure detector 10 is preferably of the indirect calorimetry type based on the measurement of the metabolism of the subject, as described for example in the above-cited U.S. Pat. Nos. 4,917,108; 5,038,792; 5,178,155; 5,179,958 and 5,836,300 as well as co-pending patent application 09/630,398. As briefly described above, and as more particularly described in those patents, such a caloric expenditure rate detector includes a respiratory gas analyzer which detects inhalations and exhalations of the subject, analyzes the oxygen consumption, and produces the caloric expenditure rate measurement from such an analysis. While such a caloric expenditure rate detector is preferred in the illustrated apparatus, it will be appreciated that other types of caloric expenditure rate detectors could be used, for example, that described in the above-cited U.S. Pat. No. 6,013,009 or in the many patents cited in the specification of that patent.

The apparatus illustrated in FIG. 1 preferably includes two types of body activity detectors, namely detector 11 which detects physical activity, such as a pedometer, or accelerometer which detects actual movements of the subject; and an exertion level detector 12 which indicates the exertion level by measuring the heart rate of the subject. Both types of body activity detectors are well known in the art.

If the illustrated apparatus is also to be used for monitoring the caloric diet of the subject, it requires an input of the caloric intake shown at 13. Such an input may be in the form of calories, or in the form of foods and quantities converted by the apparatus into calories. Both forms of caloric intakes are also known in art.

The foregoing inputs 10, 11, 12 and 13 are all inputted into a microprocessor, generally designated 20, which may be a general purpose computer, such as a personal computer (PC), a personal digital assistant (PDA) or cellular phone, etc. Microprocessor 20, however, could also be a special-purpose or dedicated computer, dedicated to perform the specific functions for monitoring the caloric expenditure rate and/or the caloric diet of the subject, as described more particularly below.

As shown in FIG. 1, microprocessor 20 includes the basic elements of a computer, namely a CPU 21, memory 22, keyboard (or other input) 23, real time clock 24, and display 25. In this case, the microprocessor also includes a mode selector 26 which enables the user to select either a Learning Mode or an Operational Mode, as will be described more particularly below. The outputs of the microprocessor 20 are generally indicated at 27, which could be a printer, display, and/or storage device, such as a storage card, disk, and the like.

As indicated above, the mode selector 26 enables the user to select either a Learning Mode or an Operational Mode. Briefly, during a Learning Mode, the microprocessor utilizes the information inputted via the detectors 10, 11, 12, for producing both a caloric expenditure rate measurement and a body activity measurement while the subject is undergoing a plurality of different body activities and at different activity rates, at least for one or more of such activities. For example, the physical activities could be walking, running, bicycling, swimming, etc. The detected physical activity could also be an inactive condition, i.e., wherein the subject is at rest or otherwise inactive. During the Learning Mode, the microprocessor computes a personal correlation factor personal to the subject, representing the correlation between the caloric expenditure rate measurement and the body activity measurement for each of the body activities and rates, and records the personal correlation factors so computed. These personal correlation factors are utilized during the operational mode to enable each subsequently measured caloric expenditure rate to be modified so that it will more accurately reflect the caloric expenditure of the respective individual required to achieve the respective body activity.

Figure 2:
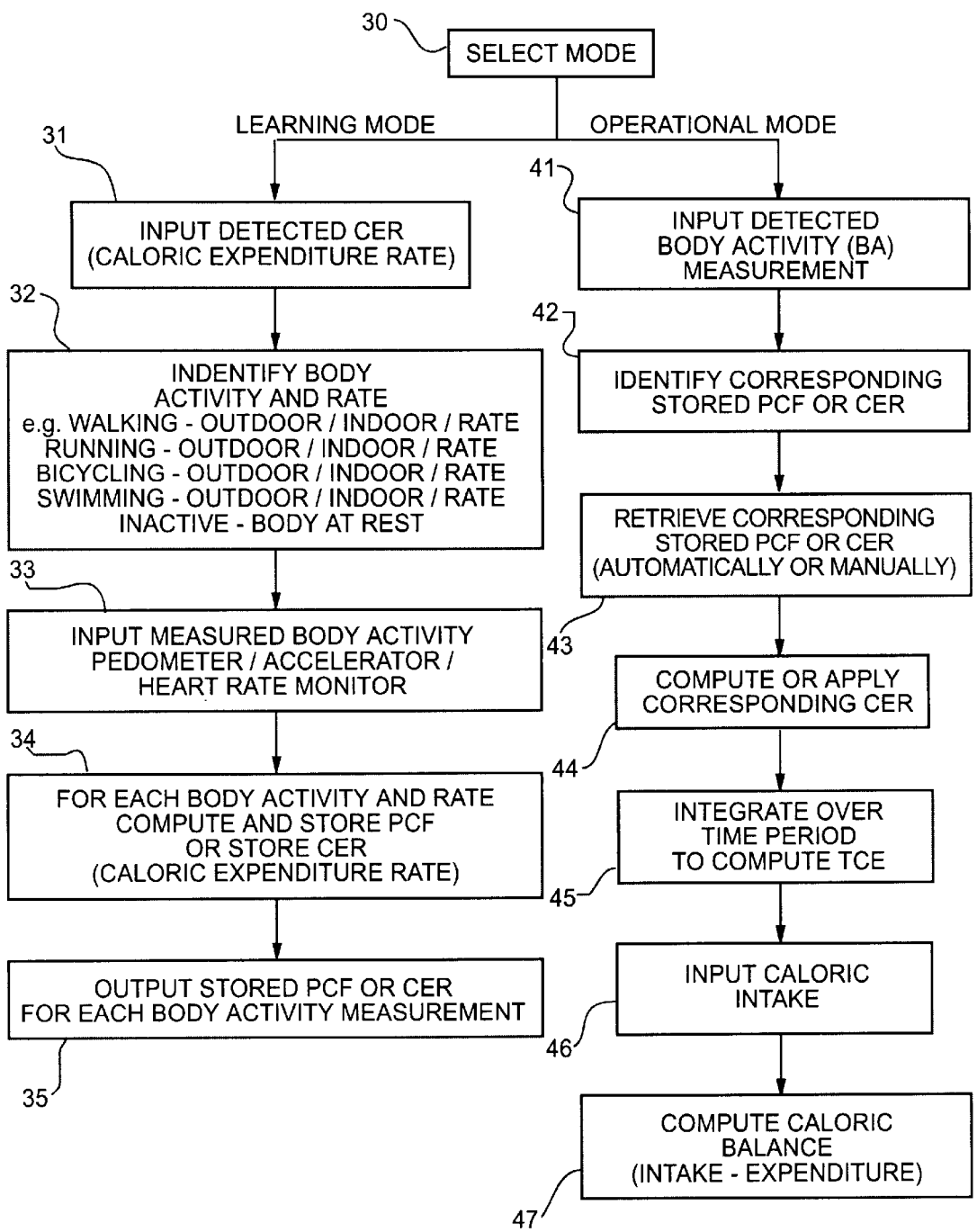
FIG. 2 is a flow chart illustrating one manner of operating the apparatus of FIG. 1.

The foregoing operation of microprocessor 20 is more particularly illustrated in the flow chart of FIG. 2. Thus, if the Learning Mode is selected (block 30) by the mode selector 26 (FIG. 1), the caloric expenditure rate of the subject is detected and inputted into the microprocessor (block 31). At the same time, the type of body activity and body activity rate are identified (block 32), and the measured body activity is inputted into the microprocessor (block 33). As shown by block 32 in FIG. 2, the various body activities and rates may include walking, running and bicycling, both outdoor and indoor, and at different rates; or swimming (identified by particular strokes and/or rates), etc. The body activity may also be an inactive or rest condition, as shown by block 32 in FIG. 2.

The body activity is measured and input into the microprocessor (block 33). The measurement of the body activity may be in any of the known manners, e.g. by a pedometer or accelerometer for measuring physical movements of the subject. The body activity could also be measured by a heart rate detector, which measures the physical exertion of the subject.

The body activity may also be measured indirectly, as by measuring the distance covered by the user during an interval of running, etc., and the time of the interval. The distance may be a known value. For runners, their caloric expenditure while running at various rates such as six, seven, eight, nine and ten miles per hour might be measured by use of an indirect calorimeter while on a treadmill. They could then run a measured distance, such as a mile or half mile, and the time required for the run measured and converted into caloric expenditure by correlation with the previous measurements.

The rate of running, biking, etc. may be measured by recording GPS measurements and the times of the measurements at intervals. The calculated speed could then be translated into caloric expenditure by correlation.

For each body activity and rate, the microprocessor computes a personal correlation factor (PCF), which is personal to that subject for the respective body activity and for the respective activity rate (block 34). The PCFs so computed, are stored, e.g. in a look-up table (LUT), or in the form of a curve, within the microprocessor. Such computed PCFs may also be stored within a removable storage device (e.g. disk, card) for application to another processor for use during the Operational Mode. Alternatively, the stored computed PCFs may be printed out to enable the subject to manually introduce this information into that microprocessor, or another microprocessor, to perform the functions effected during the Operational Mode.

During the Operational Mode, as shown in FIG. 2, the body activity rate is again detected by detector 12 while the subject is undergoing a particular body activity at a particular rate, and this measurement is introduced into the microprocessor (block 41). The identification of the body activity and rate is also introduced into the microprocessor (block 42). The personal correlation factor (PCF) computed during the Learning Mode for the respective body activity and rate is then introduced into the microprocessor (block 43). This can be done by automatically transferring the respective PCF from the microprocessor memory 22 stored to the CPU. On the other hand, if the PCFs computed during the Learning Mode are stored in a removable storage device (e.g. disk, card), such a removable storage device may be applied to the processor for introducing the respective PCF; or if the PCFs were outputted in printed form, the respective PCF may be manually introduced by the subject into the microprocessor according to block 43 in FIG. 2.

The introduced PCF for the respective body activity and rate is then utilized to compute the actual caloric expenditure rate applicable to the particular subject, for the particular body activity, at the particular activity rate (block 44), thereby providing an accurate measurement of the actual caloric expenditure rate.

The caloric expenditure rate so computed is then integrated over a time period to compute the total caloric expenditure (TCE) (block 45).

If the apparatus is also used for monitoring the caloric diet, the caloric intake is also inputted via the input unit 13 (FIG. 1), as indicated by block 46, to enable the microprocessor to produce a running balance of the caloric intake minus the caloric expenditure (block 47).

It will thus be seen, as shown in FIG. 1, the microprocessor 20 may produce any one of a number of desired outputs, including: the PCFs (personal correction factors) for the respective subject, body activity and activity rate; the CERs (caloric expenditure rates) for the respective subject, body activity and activity rate; the total calories expended (TCE); and/or the caloric balance of caloric intake less caloric expenditure. The foregoing could be outputted to output devices in the microprocessor itself, or could be outputted in various forms to printers, displays, or other forms of storage devices for application to other processors.

Figure 3:
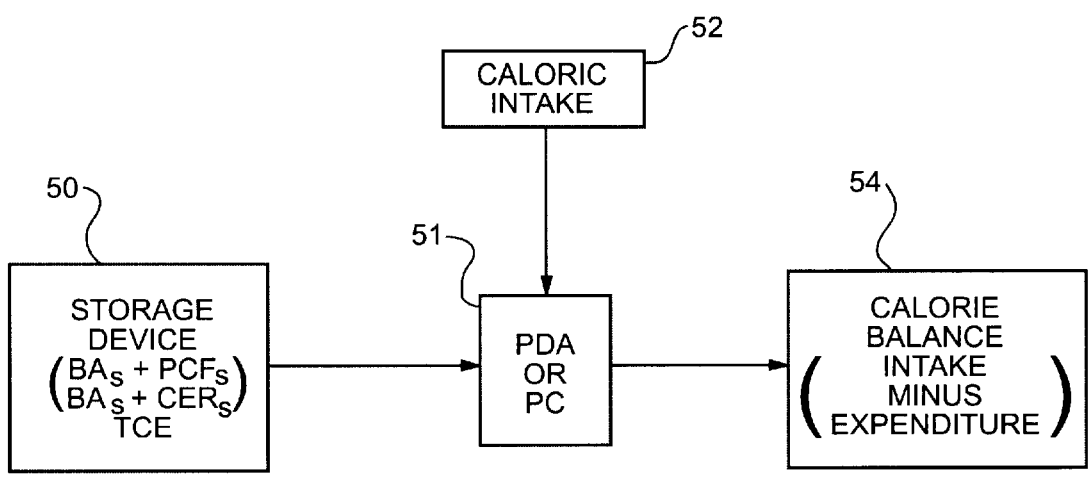
FIG. 3 is a block diagram illustrating another manner of using the apparatus of FIG. 1 with an external PDA (personal digital assistant) or PC (personal computer).

FIG. 3 illustrates the option wherein the total calories expended (TCE) is computed and is stored on a separate storage device, such as a card or disk 50, and inputted into a PDA or PC 51, together with the caloric intake over the respective period of time inputted via input device 52. The PDA or PC then processes this information to produce the caloric balance of caloric intake minus caloric expenditure, as shown by block 54.

It will be appreciated that the personal correlation factor could be stored in the form of the computed relation of the caloric expenditure rate and the body activity measured during the test mode, or in the form of the latter two measurements alone, such that when a body activity is subsequently detected corresponding to one measured during the test mode, the corresponding caloric expenditure rate measured and stored in the test mode can be retrieved or computed for use as the caloric expenditure rate in monitoring the caloric expenditure of the subject.

The described apparatus thus enables the caloric expenditure rate of a subject to be continuously monitored by using only a body activity detector, such as a pedometer, accelerometer, and/or heart rate monitor. Such body activity detectors can be more conveniently carried by the subject without interfering with the subject's normal activities (both exercising and non-exercising activities), as compared to caloric expenditure rate detectors, particularly of the respiratory type which are the preferred type in the apparatus as discussed above.

While the invention has been described with respect to a preferred embodiment, it will be appreciated that this is set forth only for purposes of example, and that many variations, modifications and other applications of the invention may be made.

What is claimed is:

1. Apparatus for monitoring the caloric expenditure rate of a subject, comprising:
    a caloric expenditure rate detector for detecting and measuring the caloric expenditure rate of the subject;
    a body activity detector for detecting and measuring the body activity of the subject; and
    a processor for storing a measured caloric expenditure rate and a concurrently measured body activity for each of a plurality of different body activities and activity rates, to enable each subsequently detected body activity measurement to be converted to the caloric expenditure rate of the respective subject.

2. The apparatus according to claim 1, wherein said processor is programmable to operate in:
    a test mode, in which the processor measures and stores a caloric expenditure rate for each body activity; and
    an operational mode, in which the processor converts each subsequently detected body activity measurement to the corresponding caloric expenditure rate stored during the test mode.

3. The apparatus according to claim 2, wherein said processor integrates the caloric expenditure rate over a period of time to produce an output representing the total caloric expenditure over the respective period of time.

4. The apparatus according to claim 1, wherein said caloric expenditure rate detector is an indirect calorimeter which detects inhalations and exhalations of the subject, analyzes the oxygen consumption, and produces said caloric expenditure rate measurement therefrom.

5. The apparatus according to claim 1, wherein said body activity detector additionally produces a body activity measurement when the body of the subject is relatively at rest, to enable a personal correlation factor also to be computed and stored during the test mode corresponding to a relatively at rest body condition of the subject, and to be used in the operational mode for determining the caloric expenditure rate when the subject's body is at rest.

6. The apparatus according to claim 1, wherein said body activity detector detects physical activities of the subject including walking and running at different rates.

7. The apparatus according to claim 1 wherein the body activity detector comprises a GPS system and a clock, means for recording the GPS output and the time intervals, and means for calculating the body speed from said recorded measurements.

8. The apparatus according to claim 1, wherein said body activity detector detects the heart rate of the subject.

9. The apparatus according to claim 1, wherein said body activity detector detects both the physical activities of the subject and the heart rate of the subject.

10. Apparatus for monitoring the caloric expenditure rate of a subject, comprising:
    a caloric expenditure rate detector for detecting and measuring the caloric expenditure rate of the subject;
    a body activity detector for detecting and measuring the body activity of the subject, including when the subject's body is relatively at rest; and
    a processor for storing a measured caloric expenditure rate and a concurrently measured body activity for each of a plurality of different body activities; said processor being programmable to operate in:
        a test mode in which the processor measures and stores a caloric expenditure rate for each body activity; and
        an operational mode in which the processor converts each subsequently detected body activity measurement to the corresponding caloric expenditure rate stored during the test mode.

11. The apparatus according to claim 10, wherein said processor integrates the caloric expenditure rate over a period of time to produce an output representing the total caloric expenditure over the respective period of time.

12. The apparatus according to claim 10, wherein said caloric expenditure rate detector is a respiratory gas analyzer which receives inhalations and exhalations of the subject, analyzes the oxygen consumption, and produces said caloric expenditure rate measurement therefrom.

13. The apparatus according to claim 10, wherein said body activity detector detects physical activities of the subject including walking and running at different rates.

14. The apparatus according to claim 10, wherein said body activity detector detects the heart rate of the subject.

15. The apparatus according to claim 10, wherein said body activity detector detects both the physical activities of the subject an d the heart rate of the subject.

16. Apparatus for monitoring the caloric expenditure rate of a subject, comprising:
    a caloric expenditure rate detector for detecting and measuring the caloric expenditure rate of a subject;
    a body activity detector for detecting and measuring the body activity of the subject; and
    a processor for storing a measured caloric expenditure rate with a measured body activity for each of a plurality of body activities during a test mode, and, in an operational mode, receiving a signal from the body activity detector and calculating the caloric expenditure utilizing the stored caloric expenditure rate corresponding to the body activity as stored in the test mode.

17. The apparatus according to claim 16, wherein said processor is a PDA (personal digital assistant).

18. The apparatus according to claim 16, wherein said processor is a PC (personal computer).

19. A method of monitoring the caloric expenditure of a subject, comprising:
    A. equipping the subject with: (1) a calorie expenditure rate detector for producing a caloric expenditure rate measurement of the subject, and (2) a body activity detector for producing a body activity measurement of the subject;
    B. during a test mode: (1) utilizing said detectors for producing said caloric expenditure rate measurement and said body activity measurement while the subject is undergoing a plurality of different body activities and at different rates, and (2) storing the correlation between said two measurements for each of said body activities and rates; and
    C. during an operational mode:
        (1) utilizing said body activity detector for producing a body activity measurement;
        (2) retrieving the corresponding caloric expenditure rate measurement stored for the respective body activity; and (3) utilizing said retrieved caloric expenditure rate measurement as the measurement of the caloric expenditure rate in monitoring the caloric expenditure of the subject.

20. The method according to claim 19, wherein said caloric expenditure rate detector is a respiratory gas analyzer which receives inhalations and exhalations of the subject, analyzes the oxygen consumption, and produces therefrom said caloric expenditure rate measurement.

21. The method according to claim 19, wherein said body activity detector also produces a measurement when the subject is relatively inactive.

22. The method according to claim 19, wherein said body activity detector detects movements of the subject.

23. The method according to claim 19, wherein said body activity detector detects the heart rate of the subject.

24. The method according to claim 19, wherein said body activity detector detects both physical movements and the heart rate of the subject.

25. A method of monitoring the caloric diet of a subject, comprising:

monitoring the caloric expenditure rate of the subject according to claim 19;

integrating the caloric expenditure rate over a period of time;

inputting the caloric intake of the subject over said period of time; and producing a running balance of the caloric intake minus the caloric expenditure.

* * * * *